(12) United States Patent
Bonrath et al.

(10) Patent No.: US 8,916,715 B2
(45) Date of Patent: Dec. 23, 2014

(54) PROCESS FOR 4-METHYLOXAZOLE-5-CARBOXAMIDE

(75) Inventors: Werner Bonrath, Basel (CH); Jocelyn Fischesser, Basel (CH); Hongyan Shen, Basel (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 14/127,610

(22) PCT Filed: May 31, 2012

(86) PCT No.: PCT/EP2012/060221
§ 371 (c)(1),
(2), (4) Date: Mar. 27, 2014

(87) PCT Pub. No.: WO2012/175304
PCT Pub. Date: Dec. 27, 2012

(65) Prior Publication Data
US 2014/0206880 A1    Jul. 24, 2014

(30) Foreign Application Priority Data
Jun. 20, 2011   (EP) .................................... 11170524

(51) Int. Cl.
*C07D 263/34* (2006.01)
*C07D 213/69* (2006.01)

(52) U.S. Cl.
CPC ............ *C07D 263/34* (2013.01); *C07D 213/69* (2013.01)
USPC .......................................................... 548/236

(58) Field of Classification Search
CPC ............................ C07D 263/48; C07D 263/34
USPC .......................................................... 548/236
See application file for complete search history.

(56) References Cited

U.S. PATENT DOCUMENTS 5,502,212 A    3/1996    Bonrath et al.

OTHER PUBLICATIONS

Stepanova, S. V.; L'vova, S. D.; Gunar, V. I. Khimiko-Farmatsevticheskii Zhurnal (1976), 10(5), 102-4.*
Rinderspacher et al., "Ueber Dipyridyl-Aehnliche Thiazolyl-Oxadole", *Helvetica Chimica Acta*, vol. 43, No. 6, Jan. 1, 1960, pp. 1522-1536.
International Search Report for PCT/EP2012/060221, mailed Aug. 23, 2012.

* cited by examiner

*Primary Examiner* — Nizal Chandrakumar
(74) *Attorney, Agent, or Firm* — Nixon & Vanderhye P.C.

(57) ABSTRACT

A process for the preparation of 4-methyl-oxazole-5-carboxamide, an intermediate in the synthesis of pyridoxine, by reacting lower alkyl 4-methyl-oxazole-5-carboxy-late with a molar excess of anhydrous, liquid ammonia.

6 Claims, No Drawings

PROCESS FOR 4-METHYLOXAZOLE-5-CARBOXAMIDE

This application is the U.S. national phase of International Application No. PCT/EP2012/060221 filed 31 May 2012 which designated the U.S. and claims priority to EP Patent Application No. 11170524.0 filed 20 Jun. 2011, the entire contents of each of which are hereby incorporated by reference.

The present invention is concerned with a novel process for the preparation of 4-methyloxazole-5-carboxamide (MOXA). This compound is a valuable intermediate in the synthesis of pyridoxine (vitamin $B_6$).

Several processes for the manufacture of pyridoxine have already been described. A summary of the most important ones is to be found, e.g., in Ullmann's Encyclopedia of Industrial Chemistry, fifth edition, 1996, vol. A 27, p. 533ff. For the industrial synthesis of pyridoxine there is now used nearly exclusively the approach described by Kondratyeva, G. Y., Khim. Nauka Promst. 2, 666 (1957), in which approach the pyridine ring is obtained by a Diels-Alder reaction of oxazoles with maleic acid or its derivatives. A particularly preferred oxazole in the synthetic pathway is 5-cyano-4-methyl-oxazole (MOXN). U.S. Pat. No. 5,910,594 describes the manufacture of 5-cyano-4-lower alkyl-oxazoles by dehydrating, in an aprotic organic solvent, a 5-carbamoyl-4-lower alkyl-oxazole with silicon tetrachloride in the presence of an amine. According to the disclosure of U.S. Pat. No. 5,502,212 OXAs are dehydrated to the corresponding OXNs by reaction of the starting material with an N,N-disubstituted formamide and cyanuric chloride in a polar, aprotic organic solvent. The yield of MOXN from the corresponding MOXA is 99.4% of the theory. Nothing, however, is disclosed on the preparation of the starting material. Although Ullmann's Encyclopedia (see above), page 533, mentions the transformation of ethyl 4-methyl-oxazole-5-carboxylate (MOXE) into MOXA no reference for this reaction comprising any reaction conditions including yield and purity is given. On the other hand U.S. Pat. No. 4,772,718 describes the one-step conversion of MOXE into MOXN in the presence of ammonia and zirconium oxide or hafnium oxide catalyst in the gas phase. With a conversion of 99% yields of 78 to 81% of MOXN are obtained. Disadvantages here are, however, the use of a relatively expensive catalyst as well as—in order to achieve an optimum reaction control—the maintenance of very precise reaction conditions. The costs for industrial production are accordingly high.

In US 2009/0036450 the production of 2-methyl-2-phenethyl-oxazole-5-carboxamide is described, wherein a solution of ethyl 4-methyl-2-phenethyl-oxazole-5-carboxylate in 7N ammonia/ethanol was stirred with a solution of 28% sodium methoxide in methanol for 7 days at room temperature. Then ammonium chloride was added and after concentration the residue was dissolved in methanol and the end product was precipitated by addition of water. The yield of the desired product was 68.0% with no indication of its purity. Such a method does not recommend itself for industrial production of large amounts of MOXA from MOXE.

It was, therefore, an object to find a method of conversion of MOXE into MOXA in high yield under attractive conditions for industrial synthesis.

In accordance with the present invention it has been found that MOXE can be converted nearly quantitatively (more than 99.0%) into MOXA with high yields (90% and more) by treatment with anhydrous, liquid ammonia.

Therefore, the present invention relates to a process for the preparation of 4-methyl-oxazole-5-carboxamide characterized by reacting lower alkyl 4-methyl-oxazole-5-carboxylate with a molar excess of anhydrous, liquid ammonia. Preferably, the reaction is carried out in the presence of a catalyst selected from the group consisting of ammonium salts, quaternary ammonium salts and alkali metal phosphates.

Lower alkyl 4-methyl-oxazole-5-carboxylates are $C_{1-6}$-alkyl esters of 4-methyl-oxazole-5-carboxylic acid. $C_{1-6}$-alky groups can be straight-chain or branched-chain groups, e.g., methyl, ethyl, n-propyl, i-propyl, n-butyl, i-butyl, tert.-butyl, pentyl and hexyl with methyl and ethyl being preferred. The esters are commercially available or can be prepared as described in, e.g., EP 27020 B1 and US 2009/0036450 or in an analogous way.

The excess, on a molar basis, of anhydrous, liquid ammonia over the oxazole-5-carboxylate should be at least 2:1 and is conveniently in the range of 5-20:1, preferably 10-15:1, more preferably 14-18:1.

The catalysts useful in the reaction of the present invention are relatively inexpensive reagents and easily since commercially available in sufficient purity. Examples of ammonium salts of formula $NH_4X$ are those wherein X is the anion of an inorganic acid such as a hydrogen halogenide, sulphuric acid and phosphoric acid or of a strong organic acid well-known in the art. In case of two- or three-basic acids mono-, di and tri-basic ammonium salts can be used as well as mixed metal/ammonium salts, the metal being, e.g., iron(II) or an alkali metal, preferably sodium or potassium. Examples of strong organic acids are carboxylic acids (mono-, di-, tri-, polybasic), such as, formic acid, acetic acid, trifluoro-acetic acid and citric acid.

Catalysts which are quaternary ammonium salts are represented by formula $[N(R^1)_3R^2]X$, wherein R1 is lower alkyl; R2 is hydrogen or lower alkyl and X is the anion of an inorganic or organic acid as defined above. Lower alkyl groups may have up to six carbon atoms with methyl and ethyl being preferred.

Alkali metal phosphates can be mono-, di- and tribasic ($MeH_2PO_4$, $Me_2HPO_4$, $Me_3PO_4$) and the metal is preferably sodium or potassium.

The preferred catalysts are ammonium halogenides (X=F, Cl, Br), ammonium chloride being particularly preferred.

The amount of catalyst in the reaction is not critical and can vary in a wide range. Preferably, it is present at least in a molar amount in the range of 0.01 to 0.5, preferably in the range of 0.025 to 0.2, relative to the oxazole-5-carboxylate.

The process is conveniently carried out under pressure and temperature conditions typical for reactions in liquid ammonia and well-known to those skilled in the art, preferably under a pressure of 5 to 20 bar (=bar absolute) and in a temperature range of 10 to 50° C.

In less than 24 hours, normally after 5 to 20 hours, the reaction is completed. The oxazole-5-carboxamide is easily isolated after evaporation of the ammonia and the mother liquor in crystalline form.

The MOXA, optionally after purification, can be converted into pyridoxine and its acid addition salts according to methods well-known in the art.

The invention is illustrated in more detail by the following examples.

General

All examples except example 35 were carried out in a 500-ml steel autoclave equipped with stirrer, pressure controller and temperature controller. All yields based on GC analysis are given in area % and correlate with yields determined by NMR analysis.

GC Analysis

GC analysis was carried out on a Hewlett-Packard HP-6850 series with split-injector and FID detector. The separation after derivatization in pyridine with BSTFA is achieved on an HP-1, dimethylpolysiloxane (30 m×320 μm, 0.25 μm) column with the following temperature program: 50° C. (0 min)→(5° C./min)→100° C. (10 min)→35° C./min→180° C. (2.2 min) 10° C./min→310° C. (13 min). Injector temperature: 250° C.; detector temperature: 300° C.

GC-MS Analysis

GC-MS analysis was carried out on a Hewlett-Packard HP-6899, MSD-5973 series system. The separation after derivatization in pyridine with BSTFA is achieved on an Rtx-5Sil MS (30 m×280 μm, 0.25 μm) column with the temperature program: 70° C. (0 min)→(10° C./min)→315° C. (15 min). The mass spectrum has been generated by electron ionization (EI).

Ammonia (Carbagas, Quality>99.98%, $H_2O$<0.01%), catalyst are commercially available and were used without further purification.

4.Methyl-oxazole-5-carboxylic acid ethyl ester (MOXE, ex. DSM Nutritional Products Grenzach, 87.8% GC) was used without further purification.

EXAMPLE 1

Preparation of MOXA (2) Catalyzed with Ammonium Chloride 59.5 g (3500 mMol) of liquid ammonia were added within 20 minutes under stirring (300 rpm) to a mixture of 44.2 g (250 mMol) of ethyl 4-methyloxazole-5-carboxylate, MOXE (1), and 0.67 g (12.5 mMol) of ammonium chloride. The internal temperature was maintained between 10° C. and 15° C. during the addition of the reactant. The reaction mixture was heated to 30° C. under 8 bara for about 20 hours, cooled down to 20° C., and the ammonia was evaporated under normal pressure within 2 hours. The reactor was purged three times with nitrogen. The crystals were filtered, washed with 20 ml of 2-propanol, and dried at 40° C., 20 mbar. The mother liquor was evaporated under reduced pressure (15 mbar, 40° C.) and the residue was dried at 40° C., 20 mbar.

Crude 2 was obtained with a purity of 99.4% ($^1$H NMR) and a yield of 96.5% based on 1.

EXAMPLES 2 AND 3

Preparation of 2 Catalyzed with Ammonium Chloride at Various Reaction Temperature Example 1 was repeated at various reaction temperatures. All yields and selectivity (Table 1) are based on 1. For better comparison the results of Example 1 were incorporated in the table.

TABLE 1

Preparation of 2 in the presence of ammonium chloride at various reaction temperatures

|  |  | Example No. | | |
|---|---|---|---|---|
|  |  | 2 | 1 | 3 |
| Reaction conditions | | | | |
| Reaction temperature | [° C.] | 20 | 30 | 35 |
| Reaction time | [h] | 20 | 20 | 20 |
| Max. pressure | [bar] | 7.2 | 8 | 8.5 |

TABLE 1-continued

Preparation of 2 in the presence of ammonium chloride at various reaction temperatures

|  |  | Example No. | | |
|---|---|---|---|---|
|  |  | 2 | 1 | 3 |
| Results | | | | |
| Conv. of 1 | [%] | 80.3 | 99.2 | 98.8 |
| Total yield based on 1 | [%] | 79.2 | 96.5 | 91.5 |
| Selectivity | [%] | 98.6 | 97.3 | 92.7 |
| Analysis of the final product | | | | |
| MOXA | [% $^1$H NMR] | 98.1 | 99.9 | 99.03 |

EXAMPLES 4 AND 5

Preparation of 2 Catalyzed with Ammonium Chloride at Various Reaction Times

Example 1 was repeated but the reaction time was varied. The results are summarized in Table 2. For better comparison the results of Example 1 are incorporated in the table.

TABLE 2

Preparation of 2 in the presence of ammonium chloride at various reaction times.

|  |  | Example No. | | |
|---|---|---|---|---|
|  |  | 4 | 5 | 1 |
| Reaction conditions | | | | |
| Reaction temperature | [° C.] | 30 | 30 | 30 |
| Reaction time | [h] | 5 | 15 | 20 |
| Max. pressure | [bar] | 8 | 8 | 8 |
| Results | | | | |
| Conv. of 1 | [%] | 73.6 | 89.0 | 99.2 |
| Total yield based on 1 | [%] | 72.5 | 86.8 | 96.5 |
| Selectivity | [%] | 98.5 | 97.5 | 97.3 |
| Analysis of the final product | | | | |
| MOXA | [% $^1$H NMR] | 99.0 | 98.5 | 99.9 |

EXAMPLES 6 AND 7

Preparation of 2 Catalyzed with Ammonium Chloride. Influence of the Excess of Ammonia Example 1 was repeated but the amount of ammonia was varied. The results are summarized in Table 3. For better comparison the results of Example 1 are incorporated in the table.

TABLE 3

Preparation of 2 in the presence of ammonium chloride with varying amount of ammonia

|  |  | Example No. | | |
|---|---|---|---|---|
|  |  | 6 | 1 | 7 |
| Reaction conditions | | | | |
| Reaction temperature | [° C.] | 30 | 30 | 30 |
| Reaction time | [h] | 20 | 20 | 20 |

TABLE 3-continued

Preparation of 2 in the presence of ammonium chloride with varying amount of ammonia

| | | Example No. | | |
|---|---|---|---|---|
| | | 6 | 1 | 7 |
| Max. pressure | [bar] | 8 | 8 | 8 |
| Ammonia | [eq.] | 10 | 14 | 18 |
| Results | | | | |
| Conv. of 1 | [%] | 80.3 | 99.2 | 99.5 |
| Total yield based on 1 | [%] | 79.2 | 96.5 | 97.5 |
| Selectivity | [%] | 98.6 | 97.3 | 98.0 |
| Analysis of the final product | | | | |
| MOXA | [% $^1$H NMR] | 98.1 | 99.9 | 99.9 |

EXAMPLE 8

Preparation of 2 Catalyzed with Ammonium Chloride. Influence of the Amount of Ammonium Chloride In the presence of 10 mol % of ammonium chloride MOXA was obtained in 94.6% yield. The results are summarized in Table 4. For better comparison the results of Example 1 are incorporated in the table.

TABLE 4

Preparation of 2 in the presence of ammonium chloride, influence of amounts of catalyst

| | | Example No. | |
|---|---|---|---|
| | | 1 | 8 |
| Reaction conditions | | | |
| Reaction temperature | [° C.] | 30 | 30 |
| Reaction time | [h] | 20 | 20 |
| Max. pressure | [bar] | 8 | 8 |
| Ammonium chloride | [eq.] | 0.05 | 0.1 |
| Results | | | |
| Conv. of 1 | [%] | 99.2 | 99.1 |
| Total yield based on 1 | [%] | 96.5 | 94.6 |
| Selectivity | [%] | 97.3 | 95.5 |
| Analysis of the final product | | | |
| MOXA | [% $^1$H NMR] | 99.9 | 98.2 |

EXAMPLE 9

Preparation of 2 Catalyzed with Ammonium Bromide

In a 500-ml steel autoclave, 44.2 g of MOXE (250 mMol) and 2.47 g (25 mMol) of ammonium bromide were cooled to 10° C. under stirring (500 rpm). When the temperature of the reaction mixture was 10° C., 59.5 g of liquid ammonia (3500 mMol) were added within 30 minutes. The internal temperature was maintained between 10° C. and 15° C. during the addition of the reactant. The reaction mixture was heated to 30° C. under 8 bara for about 20 hours, cooled down to 20° C., and the ammonia was evaporated under normal pressure within 2 hours. The reactor was purged three times with nitrogen. The crystals were filtered and dried at 40° C., 20 mbar. The mother liquor was evaporated under reduced pressure (15 mbar, 40° C.) and the residue was dried at 40° C., 20 mbar.

The result is presented in Table 5.

EXAMPLE 10

Preparation of 2 Catalyzed with Ammonium Fluoride

In a 500-ml steel autoclave, 44.2 g of MOXE (250 mMol) and 0.46 g (12.5 mMol) of ammonium fluoride were cooled to 10° C. under stirring (500 rpm). When the temperature of the reaction mixture was 10° C., 59.5 g of ammonia (3500 mMol) were added within 30 minutes. The internal temperature was maintained between 10° C. and 15° C. during the addition of the reactant. The reaction mixture was heated to 30° C. under 8 bara for about 20 hours, cooled down to 20° C., and the ammonia was evaporated under normal pressure within 2 hours. The reactor was purged three times with nitrogen. The crystals were filtered and dried at 40° C., 20 mbar. The mother liquor was evaporated under reduced pressure (15 mbar, 40° C.) and the residue was dried at 40° C., 20 mbar.

The result is presented in Table 5.

TABLE 5

Preparation of 2 catalyzed with ammonium halide salts

| | | Example No. | | |
|---|---|---|---|---|
| | | 1 | 9 | 10 |
| | | Catalyst | | |
| | | NH$_4$Cl | NH$_4$Br | NH$_4$F |
| Amount of catalyst | [eq.] | 0.05 | 0.10 | 0.05 |
| Reaction conditions | | | | |
| Reaction temperature | [° C.] | 30 | 30 | 30 |
| Reaction time | [h] | 20 | 20 | 20 |
| Max. pressure | [bar] | 8 | 8 | 8 |
| Results | | | | |
| Conv. of 1 | [%] | 99.2 | 67.7 | 93.9 |
| Total yield based on 1 | [%] | 96.5 | 62.7 | 90.0 |
| Selectivity | [%] | 97.3 | 92.6 | 95.9 |
| Analysis of the final product | | | | |
| MOXA | [% $^1$H NMR] | 99.4 | 99.9 | 97.1 |

EXAMPLE 11

Preparation of 2 Catalyzed with Ammonium Sulphate 59.5 g (3500 mMol) of liquid ammonia were added within 20 minutes under stirring (300 rpm) to a mixture of 44.2 g (250 mMol) of MOXE and 1.67 g (12.5 mMol) of ammonium sulfate. The internal temperature was maintained between 10° C. and 15° C. during the addition of the reactant. The reaction mixture was heated to 30° C. under 8 bara for about 20 hours, cooled down to 20° C. and the ammonia was evaporated under normal pressure within 2 hours. The reactor was purged three times with nitrogen. The crystals were filtered, and dried at 50° C., 20 mbar. The mother liquor was evaporated under reduced pressure (15 mbar, 50° C.) and the residue was dried at 50° C., 20 mbar.

Crude 2 was obtained with a purity of 95.7% ($^1$H NMR). The yield was 87.0% based on 1 and the selectivity 96.4%.

EXAMPLE 12

Preparation of 2 Catalyzed with Ammonium Citrate Tribasic 59.5 g (3500 mMol) of liquid ammonia were added within 30 minutes under stirring (500 rpm) to a mixture of 44.2 g (250 mMol) of MOXE and 3.13 g (12.5 mMol) of ammonium citrate tribasic. The internal temperature was maintained between 10° C. and 15° C. during the addition of the reactant. The reaction mixture was heated to 30° C. under 8 bara for about 20 hours, cooled down to 20° C. and the ammonia was evaporated under normal pressure within 2 hours. The reactor was purged three times with nitrogen. The crystals were filtered, washed with 20 ml of 2-propanol and dried at 50° C., 20 mbar. The mother liquor was evaporated under reduced pressure (15 mbar, 50° C.) and the residue was dried at 50° C., 20 mbar.

Crude 2 was obtained with a purity of 87.2% ($^1$H NMR) in 84.8% yield.

EXAMPLE 13

Preparation of 2 Catalyzed with Ammonium Acetate 59.5 g (3500 mMol) of liquid ammonia were added within 30 minutes under stirring (500 rpm) to a mixture of 44.2 g (250 mMol) of MOXE and 0.97 g (12.5 mMol) of ammonium acetate. The internal temperature was maintained between 10° C. and 15° C. during the addition of the reactant. The reaction mixture was heated to 30° C. under 8 bara for about 20 hours, cooled down to 20° C. and the ammonia was evaporated under normal pressure within 2 hours. The reactor was purged three times with nitrogen. The ethanol formed during the reaction was distilled off (80 mbar/40° C.), 100 ml of 2-propanol were added to the mixture, and the reaction mixture was stirred during 2 hours at 10° C. The crystals were filtered, washed with 20 ml of 2-propanol and dried at 50° C., 20 mbar. The mother liquor was evaporated under reduced pressure (15 mbar, 50° C.) and the residue was dried at 50° C., 20 mbar.

Crude 2 was obtained with a purity of 97.1% ($^1$H NMR) in 89% yield and 90.1% selectivity based on 1.

EXAMPLE 14

Preparation of 2 Catalyzed with Ammonium Trifluoroacetate 59.5 g (3500 mMol) of liquid ammonia were added within 30 minutes under stirring (500 rpm) to a mixture of 44.2 g (250 mMol) of MOXE and 1.67 g (12.5 mMol) of ammonium trifluoroacetate. The internal temperature was maintained between 10° C. and 15° C. during the addition of the reactant. The reaction mixture was heated to 30° C. under 8 bara for about 20 hours, cooled down to 20° C. and the ammonia was evaporated under normal pressure within 2 hours. The reactor was purged three times with nitrogen. The ethanol formed during the reaction was distilled off (80 mbar/40° C.), 100 ml of 2-propanol were added to the mixture, and the reaction mixture was stirred during 2 hours at 10° C. The crystals were filtered, washed with 20 ml of 2-propanol and dried at 50° C., 20 mbar. The mother liquor was evaporated under reduced pressure (15 mbar, 50° C.) and the residue was dried at 50° C., 20 mbar.

Crude 2 was obtained with a purity of 97.5% ($^1$H NMR) in 94.9% yield (selectivity 99.0%)/0) based on 1.

EXAMPLE 15

Preparation of 2 Catalyzed with Ammonium Iron (II) Sulfate 59.5 g (3500 mMol) of liquid ammonia were added within 30 minutes under stirring (500 rpm) to a mixture of 44.2 g (250 mMol) of MOXE and 4.9 g (12.5 mMol) of ammonium iron(II) sulfate hexahydrate. The internal temperature was maintained between 10° C. and 15° C. during the addition of the reactant. The reaction mixture was heated to 30° C. under 8 bara for about 20 hours, cooled down to 20° C. and the ammonia was evaporated under normal pressure within 2 hours. The reactor was purged three times with nitrogen. The ethanol formed during the reaction was distilled off (80 mbar/40° C.), 100 ml of 2-propanol were added to the mixture, and the reaction mixture was stirred during 2 hours at 10° C. The crystals were filtered, washed with 20 ml 2-propanol and dried at 50° C., 20 mbar. The mother liquor was evaporated under reduced pressure (15 mbar, 50° C.) and the residue was dried at 50° C., 20 mbar.

Crude 2 was obtained with a purity of 81.2% ($^1$H NMR) in 86.9% yield (90.4% selectivity) based on 1.

EXAMPLE 16

Preparation of 2 Catalyzed with Ammonium Phosphate Monobasic 59.5 g (3500 mMol) of liquid ammonia were added within 30 minutes under stirring (500 rpm) to a mixture of 44.2 g (250 mMol) of MOXE and 1.45 g (12.5 mMol) of ammonium dihydrogenphosphate. The internal temperature was maintained between 10° C. and 15° C. during the addition of the reactant. The reaction mixture was heated to 30° C. under 8 bara for about 20 hours, cooled down to 20° C. and the ammonia was evaporated under normal pressure within 2 hours. The reactor was purged three times with nitrogen. The crystals were filtered, washed with 20 ml of 2-propanol and dried at 50° C., 20 mbar for 14 hours. The mother liquor was evaporated under reduced pressure (15 mbar, 50° C.) and the residue was dried at 50° C., 20 mbar.

The results are presented in Table 6.

EXAMPLE 17

Preparation of 2 Catalyzed with Diammonium Hydrogenphosphate 59.5 g (3500 mMol) of liquid ammonia were added within 30 minutes under stirring (500 rpm) to a mixture of 44.2 g (250 mMol) of MOXE and 1.67 g (12.5 mMol) of diammonium hydrogenphosphate. The internal temperature was maintained between 10° C. and 15° C. during the addition of the reactant. The reaction mixture was heated to 30° C. under 8 bara for about 20 hours. The reaction mixture was cooled down to 20° C. and the ammonia was evaporated under normal pressure within 2 hours. The reactor was purged three times with nitrogen. The crystals were filtered, washed with 20 ml 2-propanol and dried at 50° C., 20 mbar (14 h). The mother liquor was evaporated under reduced pressure (15 mbar, 50° C.) and the residue was dried at 50° C., 20 mbar.

The results are presented in Table 6.

TABLE 6

Preparation of 2 catalyzed with ammonium phosphate salts

|  |  | Example No. 16 | Example No. 17 |
|---|---|---|---|
|  |  | Catalyst | |
|  |  | Ammonium phosphate monobasic | Ammonium phosphate dibasic |
| Amount of catalyst | [eq.] | 0.05 | 0.05 |
| Reaction conditions | | | |
| Reaction temperature | [° C.] | 30 | 30 |
| Reaction time | [h] | 20 | 20 |
| Max. pressure | [bar] | 8 | 8 |
| Results | | | |
| Conv. of 1 | [%] | 92.3 | 87.3 |
| Total yield based on 1 | [%] | 88.9 | 80.6 |
| Selectivity | [%] | 96.3 | 92.3 |
| Analysis of the final product | | | |
| MOXA | [% $^1$H NMR] | 96.6 | 90.42 |

The results are presented in Table 7.

TABLE 7

Preparation of 2 catalyzed with tetraethyl ammonium halid salts

|  |  | Example No. 18 | Example No. 19 |
|---|---|---|---|
|  |  | Catalyst | |
|  |  | Tetraethyl ammonium bromide | Tetraethyl ammonium chloride |
| Amount of catalyst | [eq.] | 0.05 | 0.05 |
| Reaction conditions | | | |
| Reaction temperature | [° C.] | 30 | 30 |
| Reaction time | [h] | 20 | 20 |
| Max. pressure | [bar] | 8 | 8 |
| Results | | | |
| Conv. of 1 | [%] | 96.0 | 95.3 |
| Total yield based on 1 | [%] | 83.2 | 74.8 |
| Selectivity | [%] | 86.6 | 90.2 |
| Analysis of the final product | | | |
| MOXA | [% $^1$H NMR] | 92.7 | 95.3 |

EXAMPLE 18

Preparation of 2 Catalyzed with Tetraethyl Ammonium Bromide 59.5 g (3500 mMol) of liquid ammonia were added within 30 minutes under stirring (500 rpm) to a mixture of 44.2 g (250 mMol) of MOXE and 2.65 g (12.5 mMol) of tetraethyl ammonium bromide. The internal temperature was maintained between 10° C. and 15° C. during the addition of the reactant. The reaction mixture was heated to 30° C. under 8 bara for about 20 hours, cooled down to 20° C. and the ammonia was evaporated under normal pressure within 2 hours. The reactor was purged three times with nitrogen. The crystals were filtered, washed with 20 ml of 2-propanol and dried at 50° C., 20 mbar, for 14 hours. The mother liquor was evaporated under reduced pressure (15 mbar, 50° C.) and the residue was dried at 50° C., 20 mbar.

The results are presented in Table 7.

EXAMPLE 19

Preparation of 2 Catalyzed with Tetraethyl Ammonium Chloride 59.5 g (3500 mMol) of liquid ammonium were added within 30 minutes under stirring (500 rpm) to a mixture of 44.2 g (250 mMol) of MOXE and 2.1 g (12.5 mMol) of tetraethyl ammonium chloride. The internal temperature was maintained between 10° C. and 15° C. during the addition of the reactant. The reaction mixture was heated to 30° C. under 8 bara for about 20 hours. The reaction mixture was cooled down to 20° C. and the ammonia was evaporated under normal pressure within 2 hours. The reactor was purged three times with nitrogen. The crystals were filtered, washed with 20 ml of 2-propanol and dried at 50° C., 20 mbar, for 14 hours. The mother liquor was evaporated under reduced pressure (15 mbar, 50° C.) and the residue was dried at 50° C., 20 mbar.

EXAMPLE 20

Preparation of 2 Catalyzed with Sodium Phosphate Monobasic 59.5 g (3500 mMol) of liquid ammonia were added within 30 minutes under stirring (500 RPM) to a mixture of 44.2 g (250 mMol) of MOXE and 1.51 g (12.5 mMol) of sodium dihydrogenphosphate. The internal temperature was maintained between 10° C. and 15° C. during the addition of the reactant. The reaction mixture was heated to 30° C. and the internal temperature was held at 30° C. under 8 bara for about 20 hours. The reaction mixture was cooled down to 20° C. and the ammonia was evaporated under normal pressure within 2 hours. The reactor was purged three times with nitrogen. The crystals were filtered and dried at 50° C., 20 mbar, for 12 hours. The mother liquor was evaporated under reduced pressure (15 mbar, 50° C.) and the residue was dried at 50° C., 20 mbar.

The results are summarized in Table 8.

EXAMPLE 21

Preparation of 2 Catalyzed Disodium Hydrogenphosphate Dibasic 59.5 g (3500 mMol) of liquid ammonium was added within 30 minutes under stirring (500 rpm) to a mixture of 44.2 g (250 mMol) of MOXE and 1.79 g (12.5 mMol) of disodium hydrogenphosphate. The internal temperature was maintained between 10° C. and 15° C. during the addition of the reactant. The reaction mixture was heated to 30° C. under 8 bara for about 20 hours. The reaction mixture was cooled down to 20° C. and the ammonia was evaporated under normal pressure within 2 hours. The reactor was purged three times with nitrogen. The crystals were filtered, washed with 20 ml of 2-propanol and dried at 50° C., 20 mbar, for 12 hours. The mother liquor was evaporated under reduced pressure (15 mbar, 50° C.) and the residue was dried at 50° C., 20 mbar.

The result is summarized in Table 8.

TABLE 8

Preparation of 2 catalyzed with sodium phosphate salts

| | | Example No. 20 | Example No. 21 |
|---|---|---|---|
| | | Catalyst | |
| | | Sodium dihydrogen-phosphate | Disodium hydrogen-phosphate |
| Amount of catalyst | [eq.] | 0.05 | 0.05 |
| Reaction conditions | | | |
| Reaction temperature | [° C.] | 30 | 30 |
| Reaction time | [h] | 20 | 20 |
| Max. pressure | [bar] | 8 | 8 |
| Results | | | |
| Conv. of 1 | [%] | 90.2 | 92.4 |
| Total yield based on 1 | [%] | 84.3 | 88.3 |
| Selectivity | [%] | 93.4 | 95.5 |
| Analysis of the final product | | | |
| MOXA | [% $^1$H NMR] | 96.65 | 92.61 |

EXAMPLE 22

Preparation of 2 Catalyzed with Potassium Dihydrogenphosphate 59.5 g (3500 mMol) of liquid ammonia were added within 30 minutes under stirring (500 rpm) to a mixture of 44.2 g (250 mMol) of MOXE and 1.71 g (12.5 mMol) of potassium dihydrogenphosphate. The internal temperature was maintained between 10° C. and 15° C. during the addition of the reactant. The reaction mixture was heated to 30° C. under 8 bara for about 20 hours. The reaction mixture was cooled down to 20° C. and the ammonia was evaporated under normal pressure within 2 hours. The reactor was purged three times with nitrogen. The crystals were filtered dried at 50° C., 20 mbar, for 12 hours. The mother liquor was evaporated under reduced pressure (15 mbar, 50° C.) and the residue was dried at 50° C., 20 mbar.

The result is summarized in Table 9.

EXAMPLE 23

Preparation of 2 Catalyzed Dipotassium Hydrogenphosphate 59.5 g (3500 mMol) of liquid ammonia were added within 30 minutes under stirring (500 rpm) to a mixture of 44.2 g (250 mMol) of MOXE and 2.20 g (12.5 mMol) of dipotassium hydrogenphosphate. The internal temperature was maintained between 10° C. and 15° C. during the addition of the reactant. The reaction mixture was heated to 30° C. under 8 bara for about 20 hours. The reaction mixture was cooled down to 20° C. and the ammonia was evaporated under normal pressure within 2 hours. The reactor was purged three times with nitrogen. The crystals were filtered, washed with 20 ml of 2-propanol and dried at 50° C., 20 mbar overnight. The mother liquor was evaporated under reduced pressure (15 mbar, 50° C.) and the residue was dried at 50° C., 20 mbar.

The result is summarized in Table 9.

TABLE 9

Preparation of 2 catalyzed with potassium phosphate salts

| | | Example No. 22 | Example No. 23 |
|---|---|---|---|
| | | Catalyst | |
| | | Potassium dihydrogen-phosphate | Dipotassium hydrogen-phosphate |
| Amount of catalyst | [eq.] | 0.05 | 0.05 |
| Reaction conditions | | | |
| Reaction temperature | [° C.] | 30 | 30 |
| Reaction time | [h] | 20 | 20 |
| Max. pressure | [bar] | 8 | 8 |
| Results | | | |
| Conv. of 1 | [%] | 92.8 | 96.0 |
| Total yield based on 1 | [%] | 86.7 | 93.8 |
| Selectivity | [%] | 93.4 | 97.7 |
| Analysis of the final product | | | |
| MOXA | [% $^1$H NMR] | 89.29 | 91.33 |

EXAMPLE 24

Preparation of 2 in Ethanol with 4 Equivalents of Ammonia without Catalyst 17.0 g (1000 mMol) of liquid ammonia were added within 20 minutes under stirring (500 rpm) to a mixture of 44.2 g (250 mMol) of MOXE and 200 ml (3430 mMol) of ethanol. The internal temperature was maintained at 5° C. during the addition of the reactant. The reaction mixture was heated to 40° C. and the internal temperature was held at 40° C. under 9.0 bars for about 20 hours. The reaction mixture was cooled down to 20° C. and the ammonia was evaporated under normal pressure within 30 minutes. The reaction mixture was cooled down to 0° C. and stirred (300 rpm) during 1 hour. The reactor was purged three times with nitrogen. The crystals were filtered, washed with 20 ml of ethanol (0° C.) and dried at 50° C., 20 mbar, for 12 hours. The mother liquor was evaporated under reduced pressure (15 mbar, 50° C.) and the residue was dried at 50° C., 20 mbar.

Crude 2 was obtained with a purity of 97.6% ($^1$H NMR) in 31.0 yield (selectivity 99.4%) based on 1.

EXAMPLES 25 TO 28

Preparation of 2 in Ethanol with 4 Equivalents of Ammonia. Influence of the Reaction Temperature without Catalyst Example 24 was repeated but the reaction temperature was varied. For a better comparison the results of example 24 were also incorporated in the following Table 10, which presents the results of examples 24 to 28.

TABLE 10

Preparation of 2 in ethanol with 4 equivalents of ammonia at various reaction temperatures

|  |  | Example No. | | | | |
| --- | --- | --- | --- | --- | --- | --- |
|  |  | 24 | 25 | 26 | 27 | 28 |
| Reaction conditions | | | | | | |
| Reaction temperature | [° C.] | 40 | 60 | 65 | 70 | 75 |
| Reaction time | [h] | 20 | 20 | 20 | 20 | 20 |
| Results | | | | | | |
| Conv. of 1 | [%] | 31.2 | 69.3 | 85.4 | 90.2 | 92.9 |
| Total yield based on 1 | [%] | 31.0 | 68.2 | 75.6 | 66.0 | 64.2 |
| Selectivity | [%] | 99.4 | 98.4 | 88.5 | 73.2 | 69.1 |
| Analysis of the final product | | | | | | |
| MOXA | [% $^1$H NMR] | 97.6 | 99.0 | 91.1 | 79.6 | 74.2 |

EXAMPLE 29

Preparation of 2 in Ethanol with 10 Equivalents of Ammonia without Catalyst 42.5 g (2500 mMol) of liquid ammonia were added within 20 minutes under stirring (500 rpm) to a mixture of 44.2 g (250 mMol) of MOXE and 200 ml (3430 mMol) of ethanol. The internal temperature was maintained at 5° C. during the addition of the reactant. The reaction mixture was heated to 40° C. under 9.0 bars for about 20 hours. The reaction mixture was cooled down to 20° C. and the ammonia was evaporated under normal pressure within 30 minutes. The reaction mixture was cooled down to 0° C. and stirred (300 rpm) during 1 hour. The reactor was purged three times with nitrogen. The crystals were filtered, washed with 20 ml ethanol (0° C.) and dried at 50° C., 20 mbar, for 14 hours. The mother liquor was evaporated under reduced pressure (15 mbar, 50° C.) and the residue was dried at 50° C., 20 mbar.

Crude 2 was obtained with a purity of 98.1% ($^1$H NMR) in 48.8% yield (selectivity 99.3%) based on 1.

EXAMPLES 30 TO 33

Preparation of 2 in Ethanol with 10 Equivalents of Ammonia. Influence of the Reaction Temperature without Catalyst Example 29 was repeated but the reaction temperature was varied. For a better comparison the results of example 29 are also incorporated in the following Table 11, which presents the results of examples 29 o 33.

TABLE 11

Preparation of 2 in ethanol with 10 equivalents of ammonia at various reaction temperatures

|  |  | Example No. | | | | |
| --- | --- | --- | --- | --- | --- | --- |
|  |  | 29 | 30 | 31 | 32 | 33 |
| Reaction conditions | | | | | | |
| Reaction temperature | [° C.] | 40 | 60 | 65 | 70 | 75 |
| Reaction time | [h] | 20 | 20 | 20 | 20 | 20 |
| Results | | | | | | |
| Conv. of 1 | [%] | 49.2 | 86.6 | 89.7 | 92.8 | 95.6 |
| Yield based on 1 | [%] | 48.8 | 76.1 | 73.5 | 67.9 | 62.1 |
| Selectivity | [%] | 99.3 | 87.9 | 81.9 | 73.2 | 65.0 |
| Analysis of the final product | | | | | | |
| MOXA | [% $^1$H NMR] | 97.6 | 91.2 | 83.0 | 78.2 | 71.7 |

EXAMPLE 34

Preparation of 2 in Anhydrous Ammonia without Catalyst 51.0 g (3000 mMol) of liquid ammonia were added within 20 minutes under stirring (500 rpm) to 44.2 g (250 mMol) of MOXE. The internal temperature was maintained at 10° C. during the addition of the reactant. The reaction mixture was heated to 30° C. (internal pressure=8.0 bars) for about 20 hours. The reaction mixture was cooled down to 20° C. and the ammonia was evaporated under normal pressure within 1 hour. The reaction mixture was cooled down to 0° C. and stirred (300 rpm) during 1 hour. The reactor was purged three times with nitrogen. The crystals were filtered, washed with 20 ml of ethanol (0° C.) and dried at 50° C., 20 mbar, for 14 hours. The mother liquor was evaporated under reduced pressure (15 mbar, 50° C.) and the residue was dried at 50° C., 20 mbar.

Crude 2 was obtained with a purity of 98.6% ($^1$H NMR) in 66.9% yield (selectivity 90.9%).

The invention claimed is:

1. A process for the preparation of 4-methyl-oxazole-5-carboxamide which comprises a step of reacting lower alkyl 4-methyl-oxazole-5-carboxylate with a molar excess of anhydrous, liquid ammonia at a temperature which is in the range of 10 to 50° C. and a pressure of 5 to 20 bara.

2. The process of claim 1 wherein the reacting step is carried out in the presence of a catalyst selected from the group consisting of ammonium salts, quaternary ammonium salts and alkali metal phosphates.

3. The process of claim 1 wherein the lower alkyl 4-methyl-oxazole-5-carboxylate is ethyl 4-methyl-oxazole-5-carboxylate.

4. The process of claim 2 wherein the catalyst is an ammonium halogenide salt.

5. The process of claim 4, wherein the catalyst is ammonium chloride.

6. The process for the preparation of vitamin $B_6$ (pyridoxine) and acid addition salts thereof, which comprises converting 4-methyl-oxazole-5-carboxamide obtained according to the process as claimed in claim 1 into pyridoxine or an acid addition salt thereof.

* * * * *